United States Patent
Hsieh

(10) Patent No.: US 10,445,886 B2
(45) Date of Patent: Oct. 15, 2019

(54) MOTION-GATED MEDICAL IMAGING

(71) Applicant: General Electric Company, Schenectady, NY (US)

(72) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 133 days.

(21) Appl. No.: 15/607,806

(22) Filed: May 30, 2017

(65) Prior Publication Data

US 2018/0350081 A1    Dec. 6, 2018

(51) Int. Cl.

| | |
|---|---|
| *G06T 7/246* | (2017.01) |
| *G06T 7/00* | (2017.01) |
| *G06T 11/00* | (2006.01) |
| *G06T 7/11* | (2017.01) |
| *A61B 6/03* | (2006.01) |
| *A61B 5/00* | (2006.01) |
| *A61B 5/11* | (2006.01) |
| *A61B 5/055* | (2006.01) |
| *A61B 6/00* | (2006.01) |
| *A61B 6/10* | (2006.01) |
| *A61B 5/113* | (2006.01) |

(52) U.S. Cl.
CPC ............ *G06T 7/248* (2017.01); *A61B 5/0064* (2013.01); *A61B 5/1121* (2013.01); *A61B 5/1122* (2013.01); *A61B 6/032* (2013.01); *G06T 7/0016* (2013.01); *G06T 7/11* (2017.01); *G06T 11/005* (2013.01); *A61B 5/055* (2013.01); *A61B 5/113* (2013.01); *A61B 5/1128* (2013.01); *A61B 5/721* (2013.01); *A61B 5/7221* (2013.01); *A61B 6/037* (2013.01); *A61B 6/102* (2013.01); *A61B 6/469* (2013.01); *A61B 6/5205* (2013.01); *A61B 6/527* (2013.01); *A61B 2505/05* (2013.01); *G06T 2207/10081* (2013.01); *G06T 2207/10088* (2013.01); *G06T 2207/20081* (2013.01)

(58) Field of Classification Search
CPC combination set(s) only.
See application file for complete search history.

(56) References Cited

U.S. PATENT DOCUMENTS

| | | | |
|---|---|---|---|
| 6,879,656 B2 * | 4/2005 | Cesmeli ................. | A61B 6/032 378/19 |
| 7,092,482 B2 * | 8/2006 | Besson ................ | A61B 6/0414 378/37 |
| 7,844,317 B2 * | 11/2010 | Salla ....................... | A61B 5/055 382/128 |
| 8,379,954 B2 * | 2/2013 | Sakaguchi ........... | A61B 6/4441 382/131 |
| 8,774,350 B2 * | 7/2014 | Tsubota ................. | A61B 6/032 378/19 |
| 8,805,037 B2 * | 8/2014 | Pack ..................... | G06T 11/006 382/128 |
| 9,165,360 B1 * | 10/2015 | Bates .................... | G06T 7/0014 |
| 9,466,132 B2 * | 10/2016 | Wollenweber ........ | G01T 1/2914 |

(Continued)

*Primary Examiner* — Anand P Bhatnagar

(57) ABSTRACT

Systems, apparatuses, and/or methods to provide motion-gated medical imaging. An apparatus may identify a data capture range of a sensor device that is to capture motion of an object during a scan process by a medical imaging device. An apparatus may identify a prescribed scan range. An apparatus may focus motion detection to a region of interest in the data capture range based on the prescribed scan range.

20 Claims, 4 Drawing Sheets

(56) References Cited

U.S. PATENT DOCUMENTS

| | | | | |
|---|---|---|---|---|
| 9,542,762 B2* | 1/2017 | Okamoto | ............... | A61B 6/032 |
| 2004/0202280 A1* | 10/2004 | Besson | ............... | A61B 6/0414 |
| | | | | 378/37 |
| 2005/0113671 A1* | 5/2005 | Salla | ............... | A61B 5/055 |
| | | | | 600/413 |
| 2005/0195937 A1* | 9/2005 | Bruder | ............... | A61B 6/032 |
| | | | | 378/19 |
| 2009/0103792 A1* | 4/2009 | Rahn | ............... | G01N 21/4795 |
| | | | | 382/131 |

* cited by examiner

MOTION-GATED MEDICAL IMAGING

TECHNICAL FIELD

Embodiments generally relate to systems, apparatuses, and/or methods to provide motion-gated medical imaging.

BACKGROUND

Medical imaging is an attractive technology to investigate disease due to relative short scanning time and reliability. A subject may be placed on a scanning table to collect a scout image followed by a final image that may be a reconstructed image from a plurality of continuous slice scans. A subject may be instructed to remain still (e.g., hold breath) during acquisition of data, although verbal instructions may be skipped when the subject is sedated. Medical imaging scans may also involve additional techniques to generate a final image including electrocardiogram (EKG) techniques, administration of imaging medication (e.g., contrast injection), and so on.

Motion by a subject or by patient table, however, may lead to collision events between a subject and a medical imaging device. In addition, motion by a subject may lead to misdiagnosis from image corruption due to motion artifacts (e.g., blur, object shape distortion, mimic of pathology, etc.). Sedation may be implemented before a scan to address motion by a subject, which may significantly impact workflow, medical risk, and cost. For example, cross-departmental cooperation may be required to ensure that a subject remains safe. In addition, a re-scan may be conducted to address motion by a subject. The re-scan may, however, waste resources since an entire area in a scan range may be re-scanned. In addition, there may be health risks from repeated beam exposure, medication exposure, etc. Also, long-term effects of re-administering a medication for a re-scan may not be completely risk-free. Post-processing (e.g., interpolation, etc.) may be used to address motion by a subject, which may impact image quality of reconstruction. Thus, there is considerable room for improvement to provide medical imaging.

DRAWINGS

The various advantages of the embodiments will become apparent to one skilled in the art by reading the following specification and appended claims, and by referencing the following drawings, in which:

DESCRIPTION

Figure 1:
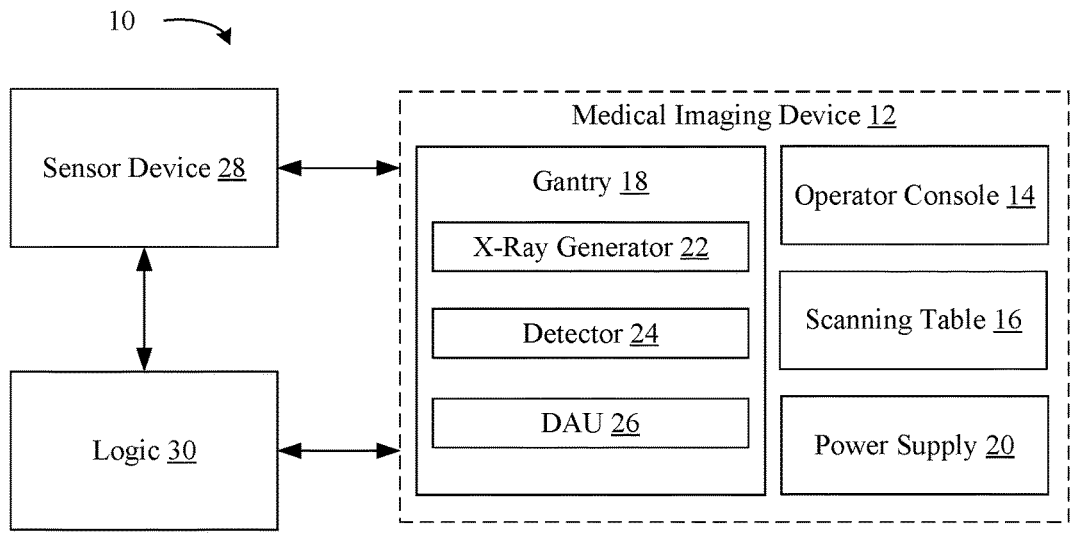
FIG. 1 is a block diagram of an example of a system to provide motion-gated medical imaging according to an embodiment.

Turning now to FIG. 1, a system 10 is shown to provide motion-gated medical imaging according to an embodiment. The system 10 includes a medical imaging device 12 which may include, for example, a computed tomography (CT) device, a positron emission tomography (PET) device, a magnetic resonance imaging (MRI) device, and so on. For example, the medical imaging device 12 may include a single photon emission CT (SPECT/CT) device, a PET/CT device, a PET/MRI device, and so on. In the illustrated example, the medical imaging device 12 includes a CT device including an operator console 14, a scanning table 16, a gantry 18, and a power supply 20.

The operator console 14 may control the operation of one or more components of the system 10 to acquire a final image of an object to be scanned. Scan parameters programmable via the operator console 14 may be specific to a type of medical imaging device used. For example, pulse sequence in an MRI scan may be programmed to obtain desired image contrast in images for tissues. In addition, scan parameters may be specific to a type of scan being implemented. For example, CT scan parameters may be specific to axial scan mode, cine scan mode, helical scan mode, dynamic scan mode, interventional mode, etc. Similarly, reconstruction and display parameters programmable via the operator console 14 may be specific to a type of medical imaging device used and/or a type of scan being implemented. For example, CT reconstruction and display parameters may include window width, window center, width of a region mapped to a reconstructed image matrix, prospective or retrospective reconstruction, sharpness or smoothness of an image, interpolation options, width of reconstructed image in z-axis, distance between two consecutive reconstructed images, rapid review options, off-center reconstruction, image filters, and so on.

A subject (e.g., a patient) may be placed on the scanning table 16 to collect a preliminary image. During acquisition of a preliminary image (e.g., a scout scan), the gantry 18 may be rotated to a fixed position and the scanning table 16 may be translated as an X-ray from an X-ray generator 22 is delivered to a detector 24 through an object being scanned. Notably, a preliminary image may provide information to guide scanning techniques such as patient-centering, automatic exposure control, protocol selection, and so on. Additionally, an operator may obtain a preliminary image and prescribe a scan range on the preliminary image. In one example, prescription on a preliminary image may define a starting location and an ending location of a scan. Thus, a preliminary image may be used to establish a scan range that is to correspond to where an object to be scanned is located, the extent of a desired axial/helical scan, etc. In one example, a preliminary image may appear similar to a radiograph. In this regard, a preliminary image may refer to a scout image and/or a CT localizer radiograph.

A preliminary image may be bypassed and/or augmented to prescribe a scan range using, for example, sensor architecture such as a sensor device 28. In one example, a pressure sensor may be located on the scanning table 16 and a user (e.g., an operator, etc.) may supply user input (e.g., a touch input, etc.) to the pressure sensor to define a starting scan location and an ending scan location. In another example, a capacitance sensor may be located on the scanning table 16 and a user may supply user input (e.g., a point gesture, etc.) to the capacitance sensor to define a starting scan location and an ending scan location. In yet another example, a camera may be located over the scanning table 16 and a user may supply a user input (e.g., a touch input, etc.) to an image of a patient and/or the scanning table 16 to define a starting scan location and an ending scan location.

A final image may then be acquired via an imaging scan. For example, a plurality of continuous slice scans may be collected around a region of a subject on the scanning table 16 using X-ray beams from the X-ray generator 22 and the detector 24. One rotation around a patient, for example, may be relatively fast (e.g., 0.28 seconds, etc.) and/or may cover a relatively large range along a patient axis (e.g., 16 cm of range, etc.). Thus, raw data for a patient (e.g., pediatric patient, etc.) may be acquired by just one rotation. X-ray data acquired by the detector 24 may be converted to light and then to electrical signals, and sent to a data acquisition unit (DAU) 26 to digitize the signals and send the digitized raw data to the operator console 14 for reconstruction. In another example, a PET detector may detect gamma rays of a radioactive material (e.g., a radiopharmaceutical, a radio tracer, etc.) administered to an object, which are converted and sent to a DAU to digitize signals for image processing. In a further example, an MRI detector may detect radio frequency (RF) signals from an object, which are converted and sent to a DAU to digitize the signals for image processing.

Accordingly, a final image may be generated by tomographic reconstruction of a series of two-dimensional (2D) X-ray images taken around an axis of rotation. A final image may include a single 2D view of a total X-ray absorption through the body along a given axis. A final image may also include a three-dimensional (3D) view from a volume built by multiplanar reconstruction, maximum-intensity projection, minimum intensity projection, etc. A final image may include, for example, an MRI image. A final image may further include, for example, a fused image. In one example, a nuclear medicine image may be superimposed with a CT image and/or a MRI image to allow for views having information from two different exams to be correlated and interpreted on one image, which may lead to more precise information and/or accurate diagnoses. A final image may be used as a diagnostic tool to diagnose various diseases, may be used as a screening or preventative tool to screen for various diseases, and so on. In one example, the operator console 14 may include a user interface such as a display (e.g., a screen, etc.) that presents a final image for diagnosis, screening, prevention, and so on.

In the illustrated system 10, the sensor device 28 may detect motion of an object to be scanned. Notably, as discussed in further detail below, the sensor device 28 may be used to monitor motion to minimize a reliance on verbal instructions used to address body motion by a subject. Additionally, the sensor device 28 may be used to monitor motion to minimize sedation of a subject used to address body motion by the subject. Also, the sensor device 28 may be used to monitor motion to trigger data acquisition that maximizes the utilization of resources and/or that maximizes image quality. The sensor device 28 may also be used to monitor motion to maximize image quality by rationally administrating medication (e.g., contrast injection when motion is minimum, etc.). The sensor device 28 may further be used to monitor motion to provide useful information in post-processing reconstruction.

Motion captured by the sensor device 28 may include body motion such as respiratory motion, head movement, arm movement, leg movement, organ movement, vasculature movement, and so on. Motion captured by the sensor device 28 may also include motion of one or more components of the medical imaging device 12 such as table motion of the scanning table 16 (e.g., table acceleration before data acquisition, table deceleration before data acquisition, etc.). Thus, the sensor device 28 may include an image capture device such as an optical camera (e.g., red, blue, green (RGB) camera), a whole body imaging camera (e.g., millimeter wave camera, etc.), a thermal camera (e.g., infrared camera, etc.), a depth camera (e.g., a three-dimensional (3D) camera, time-of-flight camera, stereo camera, etc.), and so on. In addition, the sensor device 28 may include a capacitance sensor, a resistance sensor, a piezoelectric sensor, and so on.

The illustrated system 10 may include a plurality of sensor devices. For example, a depth camera may be used with a capacitance sensor during data acquisition, two or more thermal cameras may be used during data acquisition, and so on. Additionally, a multi-dimensional (e.g., 3D) motion vector field may be generated using a plurality of motion detectors during raw data acquisition. Notably, a motion vector field may represent different aspects of an object based on a type of motion detector used. For example, a motion vector field may represent internal organ movement when a thermal camera is used, skin surface movement when an optical camera is used, and so on.

The sensor device 28 may be an external motion monitor that is coupled to one or more components of the medical imaging device 12. In addition, the sensor device 28 may be fixedly positioned and/or orientated relative to the medical imaging device 12, may be dynamically positioned and/or orientated relative to the medical imaging device 12, etc. Moreover, the position and/or orientation of the sensor device 28 may be based on a type of patient being examined, a type of scan being performed, etc. For example, a camera position may be set to around 12 o'clock for a head CT scan, while a camera position may changed to 3 o'clock or 9 o'clock for a chest/abdomen/pelvis CT scan. Thus, a plurality of sensor devices (e.g., multiple cameras, etc.) may be dynamically positioned and/or orientated around a patient to determine a most sensitive position "on the fly" and/or in real-time.

The illustrated system 10 further includes logic 30 (e.g., logic instructions, configurable logic, fixed-functionality logic hardware, etc.) configured to implement any of the herein mentioned technologies including, for example, motion-gated medical imaging. For example, the logic 30 may identify a data capture range of the sensor device 28 and focus motion detection to a region of interest (ROI) in the data capture range. The logic 30 may, for example, identify a plurality of data capture ranges from a plurality of data capture devices. In addition, the logic 30 may identify a plurality of ROIs from a single data capture range. The logic 30 may also identify a plurality of ROIs that correspond to a plurality of data capture ranges.

The logic 30 may, for example, identify a prescribed scan range on a preliminary image of an object (e.g., a scout image, etc.) and focus motion detection to an ROI in a data capture range based on the prescribed scan range. In another example, the logic 30 may identify a prescribed scan range on the scanning table 16 on which an object is located. For example, the logic 30 may identify user input (e.g., a point gesture, a touch gesture, etc.) that is to define a starting location and an ending location of a patient on the scanning table 16 and use the user input to focus motion detection.

The logic 30 may use data capture samples obtained by the sensor device 28 to detect motion. For example, the logic 30 may use an object recognition process to detect motion, may compare data capture samples to detect motion, may use a motion vector field to detect motion, and so on. The logic 30 may further determine a motion threshold for an object in an ROI and/or for an object outside of an ROI, and use a motion threshold to detect motion, to detect acceptable motion, etc.

The logic 30 may determine whether motion by an object may require a scan change (e.g., change to a prescribed scan range, to an ROI, etc.), identify whether motion by an object, a gantry (e.g., gantry tilt, etc.), and/or a scanning table may cause a collision event, verify whether an object is in a suitable posture for data acquisition, and/or determine a quiescent period of an object. The logic 30 may trigger data acquisition and/or data acquisition termination based on motion, a prescribed scan range and/or an ROI, a collision event, posture, and/or a quiescent period. In one example, an ROI may be dynamically changed during data acquisition when the scanning table travels 16 to ensure it lines up with an acquisition region. In another example, the logic 30 may use data from the sensor device 28 to predict future quiescent time-periods for data acquisition. In a further example, the logic 30 may use table motion characteristics (e.g., acceleration, deceleration, etc.) to allow the logic 30 to anticipate internal motion due to force of table acceleration, deceleration, etc. The logic 30 may also trigger medication administration (e.g., contrast injection) based on motion, a prescribed scan range and/or an ROI, a collision event, posture, and/or a quiescent period.

In one example, a comparison among data capture samples and/or an evaluation of a motion vector field by the logic 30 may be used to modulate data acquisition and/or medication administration. In addition, a comparison among data capture samples and/or an evaluation of a motion vector field may be used to compensate for motion during data acquisition (e.g., modulate data acquisition, etc.) and/or in post-processing during reconstruction to generate a final image. For example, a motion vector field from an image captured by an image capture device may provide a boundary condition for motion compensation during tomographic reconstruction. Thus, the logic 30 may provide a motion vector field to a reconstruction process to perform motion correction on the acquired data. In one example, data from the sensor device 28 may be used as input to a reconstruction process to provide motion characteristics (e.g., object motion, table motion, etc.) to be used for motion correction during reconstruction.

The logic 30 may employ machine learning and/or deep learning techniques to define and/or to refine motion sensing, prediction, data acquisition, collision avoidance, posture maintenance, medication administration, and/or image processing capabilities. For example, the logic 30 may implement machine learning as patient data increases to define and/or refine one or more of its capabilities to maximize data processing efficiency. The logic 30 may further incorporate image quality information obtained from a prior scan to modify and/or refine decision processes (e.g., motion detection, prediction, etc.). The logic 30 may also employee self-learning techniques by, for example, obtaining and updating its processes based on data collected from other motion sensing devices that are connected via an external network. An external network may include, for example, an intranet network on a different network (e.g., a different subnet, etc.), the Internet, a cloud network, etc.

The logic 30 may provide supplemental scan data to a user (e.g., a radiologist, a physician, etc.) regarding a physiological state when data acquisition was implemented. For example, the logic 30 may provide the phases of a respiratory motion cycle for a static study. In addition, the logic 30 may provide supplemental medial data regarding imaging of a moving joint, full motion cycle information for images collected at a particular time, and so on. The logic 30 may, for example, communicate supplemental medical data via the operator console 14, via a final image, via metadata corresponding to a final image, via an authorized computing platform, and so on.

In addition, the logic 30 may communicate messages such as alerts, recommendations, and so on. For example, the logic may communicate recommendations to define and/or to refine motion sensing, prediction, data acquisition, medication administration, and/or image processing capabilities. In one example, the operator console 14 may include a user interface having voice, visual, and/or text functionality to provide messages for alternative data acquisition parameters, collision alerts, and so on. A user interface may, for example, suggest that a user switch from helical data acquisition to wide-cone axial data acquisition to reduce the overall data acquisition time. Messages from the system 10 may, however, also be provided to via any authorized computing platform other than the operator console 14.

While examples have provided various components of the system 10 for illustration purposes, one or more components of the system 10 may reside in the same and/or different physical and/or virtual locations, may be combined, omitted, bypassed, re-arranged, and/or be utilized in any order. Moreover, any or all components of the system 10 may be automatically implemented (e.g., without human intervention).

Figure 2:
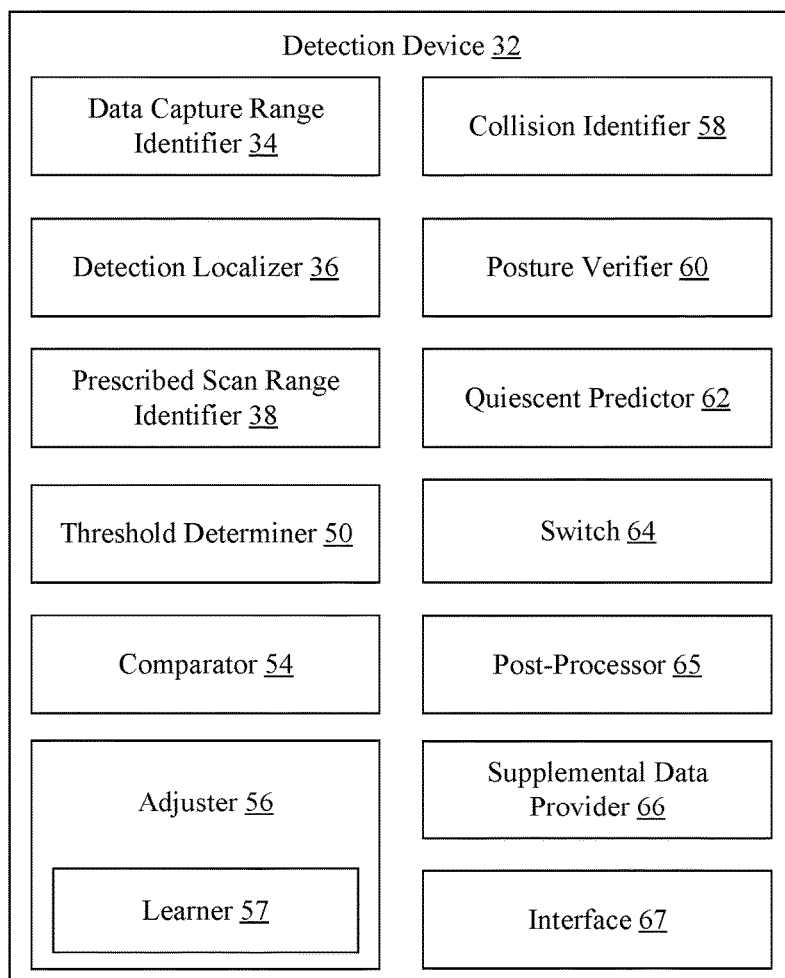
FIG. 2 is a block diagram of an example of a detection device to provide motion-gated medical imaging according to an embodiment.

FIG. 2 shows a detection device 32 to provide motion-gated medical imaging according to an embodiment. The detection device 32 may include logic similar to the logic 30 (FIG. 1). Thus, the detection device 32 may readily substitute the logic 30 in the system 10 (FIG. 1). In the illustrated example, the detection device 32 includes a data capture range identifier 34 to identify a data capture range of a sensor device that is to capture motion. A data capture range may be specific to a particular type of sensor device utilized. In one example, a data capture range may be a field of view (FOV) of an image capture device. In another example, a data capture rage may be an electric field of a surface of a capacitance sensor. Moreover, a data capture range may include a plurality of data capture ranges. For example, a data capture range may include two or more data capture ranges of a depth camera. A data capture range may include a data capture range corresponding to a sensor device of a plurality of sensor devices used to detect motion.

The detection device 32 further includes a detection localizer 36 to focus motion detection to a region of interest (ROI) in a data capture range. An ROI may include a plurality of ROIs. For example, two or more ROIs may correspond to a single data capture range. In addition, an ROI may correspond to a data capture range of a plurality of data capture ranges used to detect motion. In one example, an ROI may be set to a region within a FOV of an image capture device that corresponds to an object to be scanned such as, for example, a head, chest, pelvis, leg, organ, bone, cartilage, vasculature, neuron, portions thereof, etc. In another example, an ROI may be set to a region within an electric field of a surface of a capacitance sensor such as, for example, a guard field that shapes a sensing area electric field of a capacitance sensor.

Figure 3A:
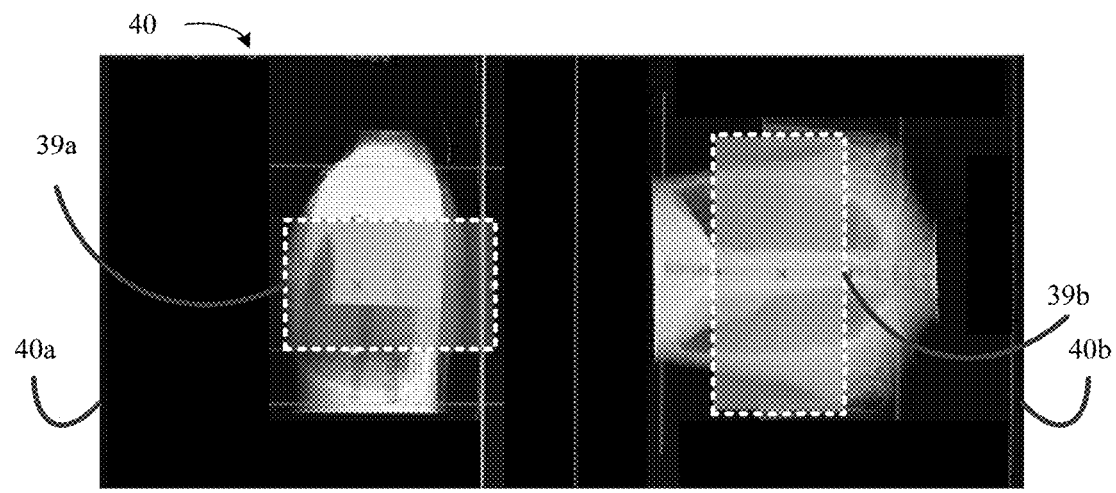
FIGS. 3A-3B are examples of images from which a region of interest in a data capture range is to be determined to focus motion detection according to an embodiment.

The detection localizer 36 may, for example, implement an object recognition technique (e.g., feature matching, etc.) to determine an ROI in a data capture range. The detection localizer 36 may also focus motion detection to an ROI in a data capture range based on a prescribed scan range. In this regard, the detection device 32 includes a prescribed scan range identifier 38 to identify a prescribed scan range. The prescribed scan range identifier 38 may, for example, identify a prescribed scan range on a preliminary image of an object (e.g., a scout image, etc.) to define a starting location and an ending location prescribed on a scout image. As shown in FIG. 3A, the prescribed scan range identifier 38 may identify a prescribed scan range 39 (39a-39b) on a preliminary image 40 (40a-40b). The prescribed scan range identifier 38 may also, for example, identify a prescribed scan range on a scanning table on which an object is located. In one example, the prescribed scan range identifier 38 may identify user input (e.g., a point gesture, a touch gesture, etc.) that is to define a starting location and an ending location of a patient on a scanning table.

Figure 3B:
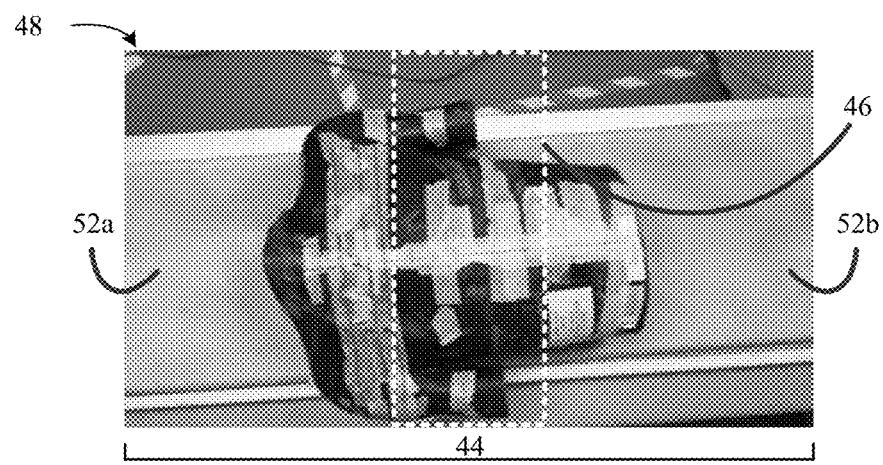

In response, for example, the detection localizer 36 may set an ROI to be an area of a FOV of an image capture device that is substantially the same as an area prescribed by a prescribed scan range, that includes in an area prescribed by a prescribed scan range (e.g., narrower, etc.), and so on. As shown in FIG. 3B, the detection localizer 36 may focus motion detection from a FOV 44 to an ROI 46 illustrated in a camera image 48. In another example, the detection localizer 36 may set an ROI to a guard field shaping a sensing area electric field of a capacitance sensor that is substantially the same as an area prescribed by a prescribed scan range, that includes in area prescribed by a prescribed scan range, and so on. For example, the detection localizer 36 may set an ROI to an area that includes maximum capacitance changes (e.g., around ears for a head scan, etc.). In a further example, the detection localizer 36 may set an ROI to an area that includes the boundaries corresponding to user input (e.g., a touch event, a gesture, etc.).

Notably, processing overhead may be minimized when an ROI is based on a prescribed scan range. For example, a buffer range may be eliminated. In this regard, an object (e.g., a liver, etc.) may shift up or down due to breathing (e.g., relative to a start position, etc.). While an operator may conventionally add a buffer to a scan range (e.g., start scan 2 cm above a top of a liver and 2 cm below a bottom of the liver, etc.), dynamic motion monitoring at an ROI may obviate a buffer since the detection device 32 is able to determine how much a subject moves.

In the illustrated example, the detection device 32 further includes a threshold determiner 50 to determine a motion threshold for an object in an ROI and/or to determine motion for an object outside of an ROI. The threshold determiner 50 may determine acceptable motion for motion of an object, unacceptable motion of an object, etc. The threshold determiner 50 may, for example, determine that sub-mm motion is more important for a head scan than for an abdomen or pelvis scan (e.g., 1 mm motion may introduce motion artifacts to cause head images to be unreliable). The threshold determiner 50 may also determine that motion sensitivity is higher for a head relative to a pelvis or abdomen since there is more dense material (e.g., bone, etc.) and/or since the size of a head may be smaller. The threshold determiner 50 may further determine that sensitivity is higher for sinuses relative to a brain.

Accordingly, the threshold determiner 50 may determine a motion threshold for an object in the ROI 46 (FIG. 3B) that is suitable to return reliable results based on a clinical application, anatomy sensitivity, and so on. The detection device 32 may further detect motion for an object outside of an ROI. For example, a patient may be instructed to hold an arm above their head during a scan of a chest while motion detection is to be focused to a center portion of a subject. When the patient has difficulty complying with the instruction, motion outside of an ROI (e.g., arm motion, etc.) may impact image quality in the center portion. Other objects that may move during a scan to impact image quality include, for example, a bag of fluid (e.g., low density material, etc.), a support structure, etc. Thus, the detection device 32 may detect motion for an object in a region 52 (52a-52b) outside of the ROI 46 while focusing motion detection in the ROI 46 (FIG. 3B) using region-based parameters such as frames per second, sampling intervals, processing cycles, resolution, capture ranges, motion thresholds, and so on.

For example, the threshold determiner 50 may select a threshold for motion of an object in a region outside of an ROI independently (e.g., same threshold, different threshold, etc.) from a threshold for motion of an object in an ROI. In addition, the threshold determiner 50 may determine a threshold for motion of an object in a region outside of an ROI based on a clinical application and/or anatomy sensitivity. For example, the threshold determiner 50 may determine that motion sensitivity is relatively high for an arm in a region outside of the ROI relative to a bag of fluid since there are sharp bony structures in an arm, which may be less sensitive than motion of an object in an ROI. The threshold determiner 50 may also account for a probability that motion of an object in a region outside of an ROI is to impact motion of an object in the ROI to return unsuitable (e.g., unreliable, etc.) results from motion artifacts. Thus, the threshold determiner 50 may set a motion threshold to indicate minimal absolute motion during each sample acquisition, minimal relative motion between each sample acquisition, etc.

The detection device 32 further includes a comparator 54 to compare data capture samples to detect motion. In one example, the comparator 54 may compare two consecutive data capture samples to detect motion. Thus, for example, a differential image may be generated that includes a difference between consecutive frames in video. Comparisons between consecutive video frames may provide information for high-frequency motion. In another example, the comparator 54 may compare a reference data capture sample with a target data capture sample to detect motion. Thus, for example, a differential image may be generated that includes a difference between non-consecutive frames in video. Comparisons between non-consecutive data capture samples may provide information for relatively slower and/or longer-term motion that may not be easily identifiable from consecutive samples.

Notably, a difference between two or more frames (e.g., a differential image) may allow for the detection of subtle changes (e.g., sub-pixel motion, fraction of a pixel size, etc.). Also, motion of images may be determined (e.g., via a subtraction result, etc.) and compared against a motion threshold to determine whether a pre-determined amount motion has been satisfied in a differential image to cause action when a motion threshold has been satisfied. For example, observed motion may be ignored when observed motion is relatively small (e.g., 0.01 mm motion in an ROI between frames, etc.). When observed motion accumulates over time, the accumulated motion may satisfy a motion threshold to cause data acquisition to be terminated, to cause a subject to be re-positioned, and so on.

In one example, the comparator 54 may utilize an initial frame as a reference frame and a current frame to detect motion from the start of a scan process to a present time. In another example, the comparator 54 may utilize a middle frame as a reference frame. For example, if there is a one-second data acquisition window, the comparator 54 may select a 0.5 s acquired frame and determine a difference in motion of one or more target frames (e.g., all other frames) to that reference frame. Thus, for example, an initial period of high motion by a patient may be ignored (e.g., acquisition not terminated, etc.) when motion is acceptable for a remainder of time during data acquisition. An early portion of data acquisition may, for example, be eliminated to generate a reliable image.

The comparator 54 may also use motion vectors to detect motion. For example, the comparator 54 may compare a motion threshold value (e.g., magnitude, direction, etc.) to a motion vector to detect motion, to determine acceptable motion, etc. A motion vector field may refer to a projection of 3D relative velocity vectors onto a 2D image plane (i.e., points on a scene moving). Thus, a motion vector field may refer to 3D velocity of a point in an image. In this regard, a motion vector field may be used to determine velocity of an object, wherein a predetermined velocity threshold may be applied to determine whether observed motion is acceptable, unacceptable, and so on.

The detection device 32 further includes an adjuster 56 to determine whether motion requires a scan change. In the illustrated example, the adjuster 56 includes a learner 57 to define and/or refine a capability of the detection device 32. Thus, the adjuster 56 and/or the learner 57 may define and/or refine a motion detection capability of the detection device 32 (e.g., ROI determination, etc.), a prediction capability of the detection device 32 (e.g., quiescent period of time, etc.), a data acquisition capability of the detection device 32 (e.g., trigger start data acquisition, etc.), a collision avoidance capability of the detection device 32 (e.g., trigger collision avoidance, etc.), a posture maintenance capability of the detection device 32 (e.g., trigger posture correction, etc.), a medication administration capability of the detection device 32 (e.g., trigger medication administration, etc.), and/or an image processing capability of the detection device 32 (e.g., reconstruction, etc.). The learner 57 may implement, for example, any input (e.g., user input, conventional technique input, etc.), to define and/or refine a capability of the detection device 32.

In one example, the adjuster 56 may determine whether motion by an object between an acquisition of a preliminary image and a data capture sample requires a change to a prescribed scan range and/or to an ROI. Accordingly, a prescribed scan range defined by a scout image may be re-adjusted if patient has moved (e.g., unacceptable motion, etc.). Moreover, a difference image based on an initial frame may be used to estimate an amount of subject positioning to be adjusted when anatomical locations have shifted between an initial scout acquisition and final image acquisition. Notably, a buffer range that accounts for a subject location shift may be obviated based on one or more adjustments.

The detection device 32 further includes a collision identifier 58 to identify when motion (e.g., by an object, etc.) is to cause a collision event. For example, a scanning table may travel during data acquisition and the collision identifier 58 may detect when there is an eminent collision between a subject and a gantry (e.g., via trajectory analysis, etc.) based on motion by an object on the scanning table, based on motion by the scanning table, and so on. Thus, a danger to a subject may be minimized when there is compensation for a collision event such as, for example, when data acquisition is automatically stopped and a subject is re-positioned.

The detection device 32 further includes a posture verifier 60 to verify whether an object is in a suitable posture for data acquisition. For example, certain protocols may expect that a subject be in a particular position (e.g., supine, prone, on side, etc.). Thus, for example, the posture verifier 60 may periodically check against a protocol to validate whether a subject is presently in an expected position for suitable data acquisition (e.g., reliable data, etc.). In this regard, reliable images may be captured when a subject is positioned in a suitable posture for data acquisition.

The detection device 32 further includes a quiescent predictor 62 to determine a quiescent period. For example, an operator may wish to acquire raw data within three breaths (e.g., when patient is in full inhalation or full exhalation, etc.). In one example, the quiescent predictor 62 may generate a motion characteristic based on historical motion data (e.g., breathing cycles, etc.) to predict a future quiescent period to capture data. The quiescent predictor 62 may also notice a pattern in repetitive motion and take into account a rate of change (e.g., acceleration is zero or close to zero, etc.). The quiescent predictor 62 may, for example, predict that a subject is going to reach a minimum motion (e.g., in 200 ms) and issue a control signal to prepare for a CT scan. The quiescent predictor 62 may further use other motion characteristics, such as table motion characteristics (e.g., acceleration, deceleration, etc.), to allow the detection device 32 to anticipate internal motion due to force of table acceleration, deceleration, etc.

The detection device 32 further includes a switch 64 to modulate acquisition of raw data. The criteria used to modulate data acquisition may depend on many factors, such as duration of data acquisition, gantry rotation speed, mode, helical pitch, registration between slabs, and so on. In this regard, motion by an object (e.g., chest, etc.) between the two scans may cause a mis-registration that leads to motion artifacts (e.g., mimic pathology when a rib appears sheered with stacked artifacts, etc.). Thus, the switch 64 may trigger data acquisition based on an entry to a quiescent period, acceptable motion (e.g., by an object, by a component of a medical imaging device such as a scanning table, etc.), compensation for a collision event, and/or suitable posture.

The switch 64 may, for example, trigger data acquisition when a breathing cycle is restored to a previous point in the cycle (e.g., minimum acceleration, minimum velocity, same velocity, etc.) where data was previously acquired before a new data capture sample is to be acquired. Accordingly, motion artifacts may be minimized when samples are captured at a same or similar point in a motion cycle (e.g., during a quiescent period, etc.), when a data capture sample does not satisfy a maximum motion threshold, and so on. In one example, slab mis-registration due to patient motion may be minimized in multi-slab axial acquisition. For example, a camera may have an entire acquisition ROI within its FOV and camera images taken during a previous slab acquisition and a current slab acquisition may be compared to ensure minimal misalignment between the two acquisitions. That is, in addition to minimal absolute motion during each slab acquisition, minimal relative motion between slab acquisitions may also be enforced.

The switch 64 may also trigger termination of data acquisition based on an exit from a quiescent period, unacceptable motion, an eminent collision event, and/or unsuitable posture. For example, data acquisition may be terminated when significant motion (e.g., based on a motion threshold, etc.) is detected during a scan. In one example where a 0.28 second gantry rotation is used to complete one acquisition, an X-ray generator may be suspended 0.05 seconds into data acquisition when significant motion is detected. The region may then be re-scanned when motion is subsided.

In this regard, data acquisition may not be repeated for an entire scan range. Data acquisition may, for example, be triggered only for a portion that is corrupted by motion. In this example, rather than re-scanning with an additional full dose, data acquisition may be suspended at 0.05 s so there is minimal waste of dose. When a quiescent period is expected, an X-ray generator is allowed to continue. Thus, a complete good total data acquisition (e.g., complete good set of data, etc.) is achieved that saves dose. Such an approach may also avoid unnecessary patient call-back.

Similarly, data acquisition may not need to be repeated for an entire scan range when there is a collision avoidance and/or posture correction. For example, when a collision event is detected during a chest-abdomen-pelvis scan, data acquisition may be terminated and a subject re-arranged to avoid the collision. Data acquisition may then be re-started. Moreover, a scan may continue to finish the rest of the scan range when there is a relatively small overlap (e.g., 2 cm overlap, etc.) between a previous scan (e.g., chest) and a current scan (e.g., abdomen/pelvis). An entire region covered by a prior scan, however, may be re-scanned when the region of collision and/or unacceptable posture is of high sensitivity (e.g., where importance and/or accuracy is high, etc.).

Moreover, motion gating may dictate when medication is to be administered (e.g., iodine in a vasculature scan, etc.). In one example, there may be a relatively short period of time to acquire raw data where injection contrast is at a maximum. Thus, motion gating may dictate when to start injecting contrast in a region so that it is not injected too early or too late due to motion (e.g., subject motion, contrast agent motion, etc.). For example, the switch 64 may obtain a time between injection and time of data acquisition (e.g., 2 s), and also obtain a prediction of a next quiescent period (e.g., 5 seconds). In this example, the switch 64 may trigger injection at 3 s so when 5 s is reached, a subject will not be moving and contrast concentration will be at maximum level to acquire data (e.g., a data capture sample, an image, a signal, etc.).

The detection device 32 further includes a post-processor 65 to compensate for motion after data acquisition. For example, the post-processor 65 may compensate for motion of an object during tomographic reconstruction. In one example, motion between the two consecutive data acquisitions that causes a misalignment (e.g., mis-registration, etc.) may be calculated and the post-processor 65 may make an adjustment in reconstruction when there is residual motion and/or when images cannot be acquired in complete register. The post-processor 65 may, for example, detect up and down motion (e.g., breathing, etc.) and correct for the up and down motion in tomographic reconstruction. In another example, the post-processor 65 may use a motion vector field for motion compensation during the tomographic reconstruction.

The detection device 32 further includes a supplemental data provider 66 to provide supplemental scan data. In one example, the supplemental scan data may include medical data regarding a physiological state when data acquisition was implemented. The supplemental data provider 66 may, for example, provide the phases of a respiratory motion cycle for a static study. In addition, the supplemental data provider 66 may provide supplemental medial data regarding imaging of a moving joint, full motion cycle information for images collected at a particular time, and so on.

The detection device 32 further includes an interface 67 that may interface with memory (e.g., cache, random access memory, etc.), with a hard drive (e.g., on-platform storage, removable storage, etc.), and so on. The interface 67 may further interface with communication functionality for a wide variety of purposes such as, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications), LiFi (Light Fidelity, e.g., Institute of Electrical and Electronics Engineers/IEEE 802.15-7, Wireless Local Area Network/LAN Medium Access Control (MAC) and Physical Layer (PHY) Specifications), 4G LTE (Fourth Generation Long Term Evolution), Bluetooth (e.g., Institute of Electrical and Electronics Engineers/IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), NFC (Near Field Communication, ECMA-340, ISO/IEC 18092), and other radio frequency (RF) purposes. The interface 67 may also interface with an input/output device such as, for example, a display, a mouse, etc. Thus, one or more components of the detection device 32 may utilize the interface 32 to provide access to data to/from one or more components thereof.

While examples have provided various components of the detection device 32 for illustration purposes, one or more components of the detection device 32 may reside in the same and/or different physical and/or virtual locations, may be combined, omitted, bypassed, re-arranged, and/or be utilized in any order. Moreover, any or all components of the detection device 32 may be automatically implemented (e.g., without human intervention).

Figure 4:
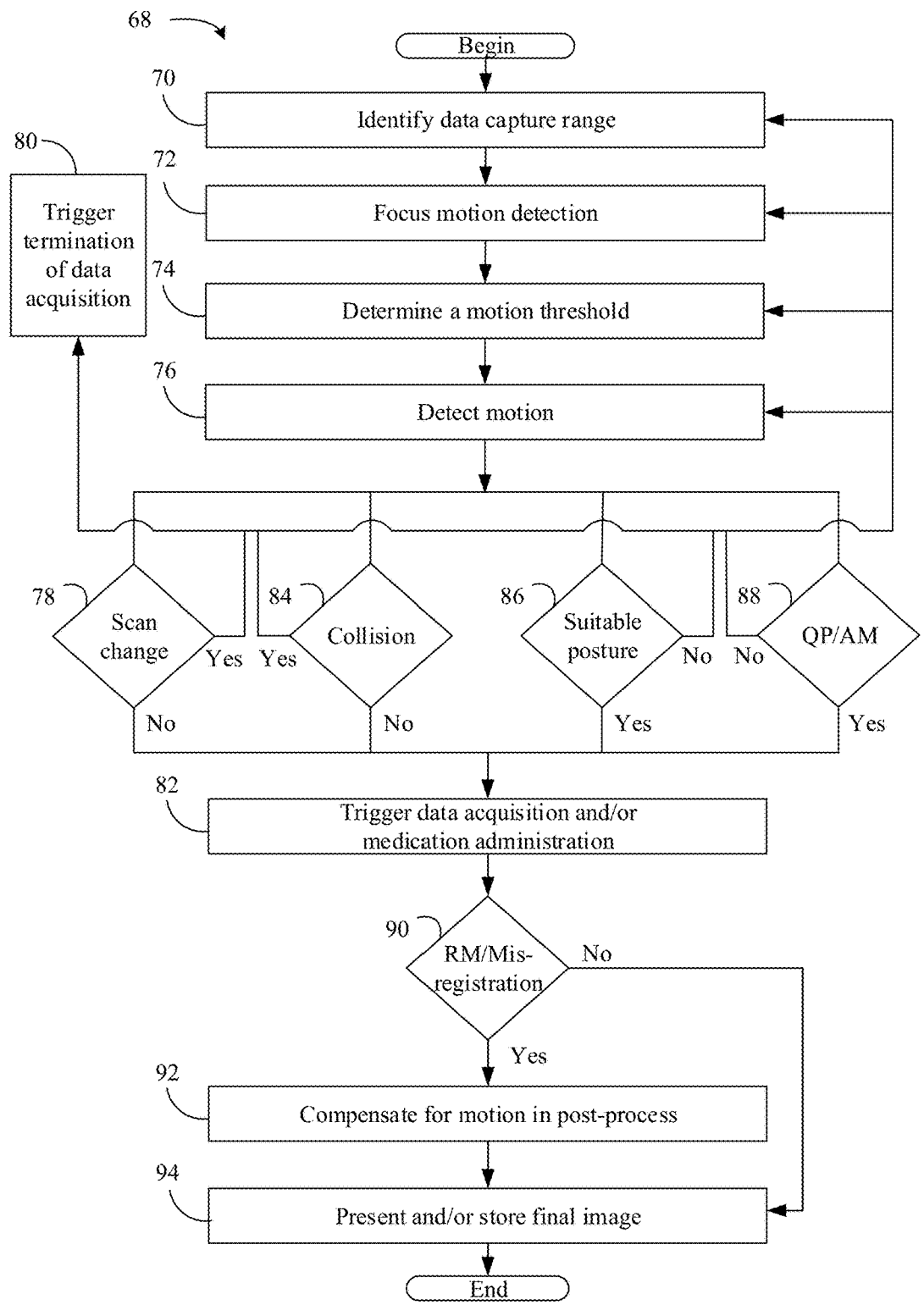
FIG. 4 is a flowchart of an example of a method to provide motion-gated medical imaging according to an embodiment.

Turning now to FIG. 4, a method 68 is shown to provide motion-gated medical imaging according to an embodiment. The method 68 may be implemented via the system 10 (FIG. 1) and/or via the detection device 32 (FIG. 2), already discussed. The method 68 may be implemented as a module or related component in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

For example, computer program code to carry out operations shown in the method 68 may be written in any combination of one or more programming languages, including an object oriented programming language such as JAVA, SMALLTALK, C++ or the like and conventional procedural programming languages, such as the "C" programming language or similar programming languages. Additionally, logic instructions might include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

Illustrated processing block 70 provides for identifying a data capture range of a sensor device that captures motion, such as motion of an object to be scanned, motion of a component of a medical imagining device, motion of an object coupled to an object to be scanned, and so on. For example, the sensor device may capture motion of a part of a patient during a scan process by a medical imaging device. A data capture range may include a plurality of data capture ranges from a plurality of motion devices.

Illustrated processing block 72 provides for focusing motion detection. Block 72 may, for example, focus motion detection to a region of interest (ROI) in a data capture range based on a prescribed scan range. Block 72 may, for example, identify a prescribed scan range (e.g., based on a preliminary image, based on a location of an object to a component of the medical imaging device, etc.) and focus motion detection to an ROI in a data capture range based on the prescribed scan range. Block 72 may also utilize an object recognition process to determine an ROI, and focus motion detection to the ROI based on object recognition.

Illustrated processing block 74 provides for determining a motion threshold. Block 74 may, for example, determine a first threshold for motion in an ROI and/or determine a second threshold for motion in a restricted region outside of an ROI. In one example, a first threshold and a second threshold may be independently selected. Moreover, a first threshold and a second threshold may independently be based on a clinical application, anatomy sensitivity, and so on. A threshold (e.g., based on motion character, etc.) may be a binary rule such as motion/no motion. A threshold may be determined from a curve (e.g., a 3D curve, etc.) that shows how much a patient moved as a function of time. A threshold may include a velocity threshold, an acceleration threshold, a distance threshold, a magnitude threshold, and so on.

Illustrated processing block 76 provides for detecting motion. Block 76 may detect motion in an ROI, in a restricted region outside of an ROI, and so on. Block 76 may compare two consecutive data capture samples to detect motion. In addition, block 76 may compare a reference data capture sample with a target data capture sample to detect motion. Block 76 may also utilize a vector motion field to detect motion. In addition, block 76 may utilize optical flow to detect motion. For example, block 76 may determine observed 2D displacement of brightness patterns in image to detect motion. Block 76 may utilize an object recognition process to detect motion.

A determination may be made at block 78 whether motion (e.g., by an object, etc.) is to require a scan change (e.g., to a prescribed scan range, to an ROI, etc.). If so, then the method 68 may revert to any of the blocks 70-76. In addition, illustrated processing block 80 may trigger termination of data acquisition. If motion by is not to require a change, or if corrective action is taken to make an adjustment (e.g., to a prescribed scan range, to an ROI, etc.) then illustrated processing block 82 may trigger data acquisition and/or may trigger medication administration.

Additionally, a determination may be made at block 84 whether motion (e.g., by an object, etc.) is to cause a collision event. If so, then the method 68 may revert to any of the blocks 70-76. In addition, block 80 may trigger termination of data acquisition. If motion is not to cause a collision event, or if corrective action is taken to compensate for a collision event, then block 82 may trigger data acquisition and/or may trigger medication administration.

Additionally, a determination may be made at block 86 whether an object is in a suitable posture. If not, then the method 68 may revert to any of the blocks 70-76. In addition, block 80 may trigger termination of data acquisition. If an object is in a suitable posture, or if corrective action is taken to place an object in a suitable posture, then block 82 may trigger data acquisition and/or may trigger medication administration.

Additionally, a determination may be made at block 88 whether a quiescent period (QP) (e.g., of an object, etc.) is detected (e.g., entered, approaching, etc.) and/or whether acceptable motion (AM) is detected. If not, then the method 68 may revert to any of the blocks 70-76. In addition, block 80 may trigger termination of data acquisition. If a quiescent period of is detected and/or acceptable motion is detected, then block 82 may trigger data acquisition and/or may trigger medication administration.

A determination may be made at block 90 whether residual motion (RM) is observed and/or whether images cannot be acquired in predetermined register. If so, then illustrated processing block 92 may compensate for motion in post-processing. Block 92 may correct for up and down motion in reconstruction. Block 92 may also use a motion vector field for motion compensation during reconstruction to generate motion compensated reconstructions. Reconstruction may include, for example, filtered backprojection reconstruction, iterative reconstruction, and so on. Thus, location parameters of a reconstructed point may be superimposed by block 92 with a calculated motion vector to reconstruct a motion compensated image. Block 92 may also, for example, detect how much a subject has moved during data acquisition and generate a motion curve as a function of time that may be used to compensate for that motion, If residual motion is not observed and/or if images are acquired in acceptable register, or if there is motion compensation, then illustrated processing block 94 presents and/or stores a final image. The final image may be retrieved from a data store (e.g., memory, etc.) and presented to a user (e.g., via a display, etc.). The final image may be used in therapeutic applications such as disease screening, disease diagnosis, and so on.

While independent blocks and/or a particular order has been shown for illustration purposes, one or more of the blocks of the method 68 may be combined, omitted, bypassed, re-arranged, and/or flow in any order. Moreover, any or all blocks of the method 68 may be automatically implemented (e.g., without human intervention).

In addition, any or all of the blocks of the method 68 may include further operations such as placing a patient on a scanning table, assisting patent positions with a detector device (e.g., a camera, etc.), monitoring and/or analyzing motion patterns with images, conducting a scout scan and/or defining a scan range, incorporating a scan range into a region of interest, generating motion characteristics (e.g., breathing, quiescent time, amount of motion as a function of time, magnitude of motion, etc.) in a scan range and/or in an outer range (e.g., corresponding to a region outside of a region of interest, etc.), re-adjusting a scan range (e.g., based on an initial-frame difference image, etc.), predicting a quiescent period, triggering data acquisition, continuing to monitor motion and/or taking corrective action during a scan, providing motion vectors for acquisition period and/or performing motion correction, and so on.

In another example, output from a sensor device (e.g., camera, etc.) may be used to generate an outline of a subject if a subject is outside of a field of view to help acquisition, reconstruction, and so on. In a further example, machine learning may be used to define and/or refine a motion detection capability, a prediction capability, an acquisition capability, a collision avoidance capability, a posture maintenance capability, a medication administration capability, and/or an image processing capability. For example, the method 68 may employee self-learning techniques by obtaining and updating its processes based on data collected from other motion sensing devices that are connected via an external network. Moreover, supplemental data may be provided to a user such as, for example, a breathing cycle, etc.

Additionally, a notification may be provided to a user that is to relate to a motion detection capability, a prediction capability, an acquisition capability, a collision avoidance capability, a posture maintenance capability, a medication administration capability, and/or an image processing capability. For example, an alert may be issued that is to indicate an ROI needs to be adjusted, a quiescent period is to approach, a collision event needs to be avoided, posture needs to be corrected, motion compensation is to be implemented in a post-process, and so on. In another example, a recommendation may be issued that is to provide guidance regarding adjustment of an ROI, configuration of a quiescent period, avoidance of a collision event, correction of posture, reconstruction parameters, and so on.

Figure 5:
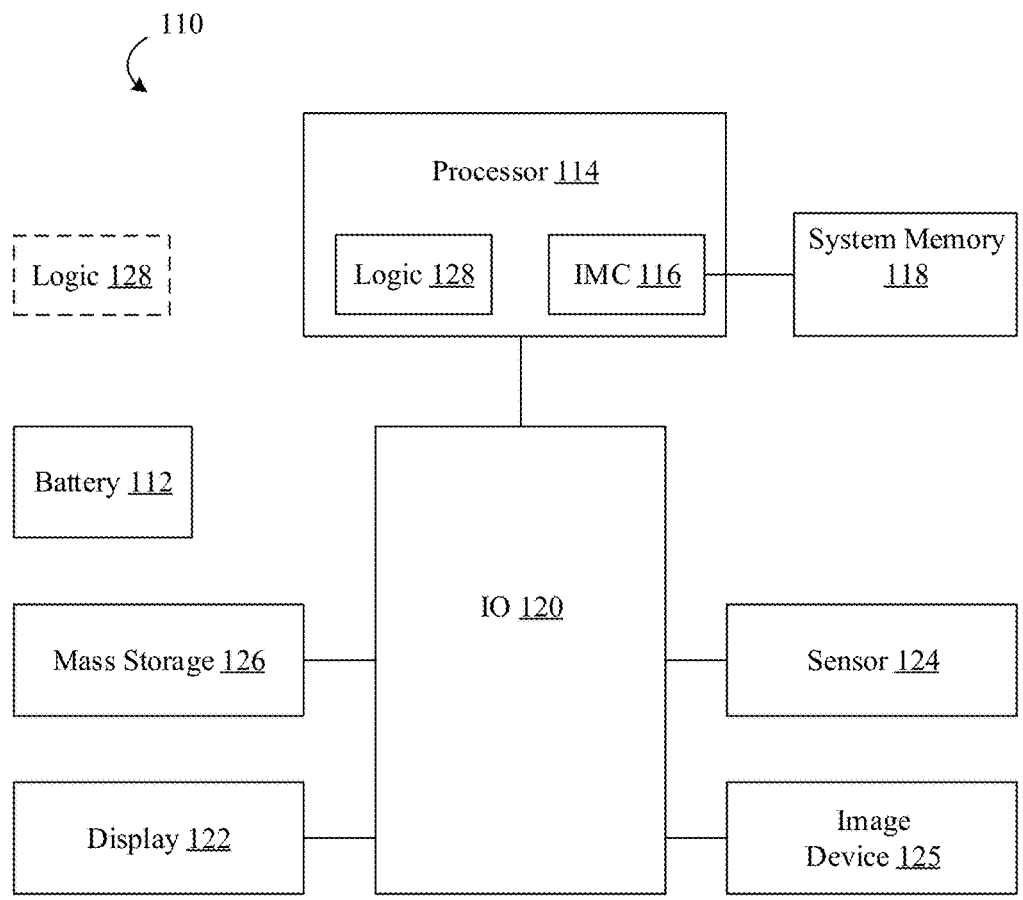
FIG. 5 is a block diagram of an example of a computing device to provide motion-gated medical imaging according to an embodiment.

FIG. 5 shows a computing device 110 according to an embodiment. The computing device 110 may be part of a platform having computing functionality, communications functionality, imaging functionality, or any combination thereof. In the illustrated example, the device 110 includes a battery 112 to supply power to the device 110 and a processor 114 having an integrated memory controller (IMC) 116, which may communicate with system memory 118. The system memory 118 may include, for example, dynamic random access memory (DRAM) configured as one or more memory modules such as, for example, dual inline memory modules (DIMMs), small outline DIMMs (SODIMMs), etc.

The illustrated device 110 also includes a input output (IO) module 120, sometimes referred to as a Southbridge of a chipset, that functions as a host device and may communicate with, for example, a display 122 (e.g., touch screen, flexible display, liquid crystal display/LCD, light emitting diode/LED display), a sensor 124 (e.g., touch sensor, an antenna sensor, an accelerometer, GPS, a biosensor, etc.), an image device 125 (e.g., a camera, etc.), and mass storage 126 (e.g., hard disk drive/HDD, optical disk, flash memory, etc.). The processor 114 and the IO module 120 may be implemented together on the same semiconductor die as a system on chip (SoC).

The illustrated processor 114 may execute logic 128 (e.g., logic instructions, configurable logic, fixed-functionality logic hardware, etc., or any combination thereof) configured to implement any of the herein mentioned processes and/or technologies, including the system 10 (FIG. 1), the detection device 32 (FIG. 2), the images 40, 48 (FIGS. 3A-3B), and/or one or more blocks of the method 68 (FIG. 4), discussed above. In addition, one or more aspects of the logic 128 may alternatively be implemented external to the processor 114. Thus, the computing device 110 may provide motion-gated medical imaging.

ADDITIONAL NOTES AND EXAMPLES

Example 1 may include an apparatus to provide motion-gated medical imaging comprising a data capture range identifier to identify a data capture range of a sensor device that is to capture motion of an object during a scan process by a medical imaging device, a prescribed scan range identifier to identify a prescribed scan range, and/or a detection localizer to focus motion detection to a region of interest in the data capture range based on the prescribed scan range.

Example 2 may include the apparatus of Example 1, wherein the prescribed scan range identifier is to identify a scan range to be prescribed on one or more of a preliminary image of the object or a scanning table on which the object is located.

Example 3 may include the apparatus any one of Examples 1 to 2, further including a threshold determiner to, determine a first threshold for motion in the region of interest, and/or determine a second threshold for motion in a restricted region outside of the region of interest, wherein the first threshold and the second threshold are to be independently selected and are to be independently based on one or more of a clinical application or anatomy sensitivity.

Example 4 may include the apparatus of any one of Examples 1 to 3, further including a comparator to, compare two consecutive data capture samples to detect motion, and/or compare a reference data capture sample with a target data capture sample to detect motion.

Example 5 may include the apparatus of any one of Examples 1 to 4, further including an adjuster to determine whether motion by one or more of the object or a component of the medical imaging device is to require a change to one or more of the prescribed scan range or the region of interest, a collision identifier to identify whether motion by one or more of the object or the component of the medical imaging device is to cause a collision event, a posture verifier to verify whether the object is to be in a suitable posture, and/or a quiescent predictor to determine a quiescent period of the object.

Example 6 may include the apparatus of any one of Examples 1 to 5, further including a switch to, trigger data acquisition based on one or more of an entry to a quiescent period, acceptable motion, compensation for a collision event, or suitable posture, and/or trigger termination of the data acquisition based on one or more of an exit from the quiescent period, unacceptable motion, a failure to compensate for the collision event, or unsuitable posture.

Example 7 may include the apparatus of any one of Examples 1 to 6, wherein the switch is to trigger medication administration based on one or more of an entry to a quiescent period, acceptable motion, compensation for a collision event, or suitable posture.

Example 8 may include the apparatus of any one of Examples 1 to 7, further including a post-processor to compensate for motion of the object to reconstruct the object and generate a final image, a learner to define and/or refine one or more of a motion detection capability, a prediction capability, an acquisition capability, a collision avoidance capability, a posture maintenance capability, a medication administration capability, or an image processing capability, a supplemental data provider to provide supplemental data to a user, and/or a communicator to provide a message to the user that is to relate to one or more of the motion detection capability, the prediction capability, the acquisition capability, the collision avoidance capability, the posture maintenance capability, the medication administration capability, or the image processing capability.

Example 9 may include the apparatus of any one of Examples 1 to 8, further including a plurality of detector devices external to the medical imaging device, wherein at least one detector device of the plurality of detector devices is to be used to generate one or more of a plurality of data capture ranges, a plurality of regions of interest, or a multi-dimensional motion vector field.

Example 10 may include at least one computer readable storage medium comprising a set of instructions, which when executed by a processor, cause the processor to identify a data capture range of a sensor device that is to capture motion of an object during a scan process by a medical imaging device, identify a prescribed scan range, and/or focus motion detection to a region of interest in the data capture range based on the prescribed scan range.

Example 11 may include the at least one computer readable storage medium of Example 10, wherein the instructions, when executed, cause the processor to identify a scan range to be prescribed on one or more of a preliminary image of the object or a scanning table on which the object is located.

Example 12 may include the at least one computer readable storage medium of any one of Examples 10 to 11, wherein the instructions, when executed, cause the processor to determine a first threshold for motion in the region of interest, and/or determine a second threshold for motion in a restricted region outside of the region of interest, wherein the first threshold and the second threshold are to be independently selected and are to be independently based on one or more of a clinical application or anatomy sensitivity.

Example 13 may include the at least one computer readable storage medium of any one of Examples 10 to 12, wherein the instructions, when executed, cause the processor to compare two consecutive data capture samples to detect motion, and/or compare a reference data capture sample with a target data capture sample to detect motion.

Example 14 may include the at least one computer readable storage medium of any one of Examples 10 to 13, wherein the instructions, when executed, cause the processor to determine whether motion by one or more of the object or a component of the medical imaging device is to require a change to one or more of the prescribed scan range or the region of interest, identify whether motion by one or more of the object or the component of the medical imaging device is to cause a collision event, verify whether the object is to be in a suitable posture, and/or determine a quiescent period of the object.

Example 15 may include the at least one computer readable storage medium of any one of Examples 10 to 14, wherein the instructions, when executed, cause the processor to trigger data acquisition based on one or more of an entry to a quiescent period, acceptable motion, compensation for a collision event, or suitable posture, and/or trigger termination of the data acquisition based on one or more of an exit from the quiescent period, unacceptable motion, a failure to compensate for the collision event, or unsuitable posture.

Example 16 may include the at least one computer readable storage medium of any one of Examples 10 to 15, wherein the instructions, when executed, cause the processor to trigger medication administration based on one or more of an entry to a quiescent period, acceptable motion, compensation for a collision event, or suitable posture.

Example 17 may include the at least one computer readable storage medium of any one of Examples 10 to 16, wherein the instructions, when executed, cause the processor to compensate for motion of the object to reconstruct the object and generate a final image, define and/or refine one or more of a motion detection capability, a prediction capability, an acquisition capability, a collision avoidance capability, a posture maintenance capability, a medication administration capability, or an image processing capability, provide supplemental data to a user, and/or provide a message to the user that is to relate to one or more of the motion detection capability, the prediction capability, the acquisition capability, the collision avoidance capability, the posture maintenance capability, the medication administration capability, or the image processing capability.

Example 18 may include the at least one computer readable storage medium of any one of Examples 10 to 17, wherein the instructions, when executed, cause the processor to utilize a plurality of detector devices external to the medical imaging device, wherein at least one detector device of the plurality of detector devices is to be used to generate one or more of a plurality of data capture ranges, a plurality of regions of interest, or a multi-dimensional motion vector field.

Example 19 may include a method to provide motion-gated medical imaging comprising identifying a data capture range of a sensor device that captures motion of an object during a scan process by a medical imaging device, identifying a prescribed scan range, and/or focusing motion detection to a region of interest in the data capture range based on the prescribed scan range.

Example 20 may include the method of Example 19, further including identifying a scan range prescribed on one or more of a preliminary image of the object or a scanning table on which the object is located.

Example 21 may include the method of any one of Examples 19 to 20, further including determining a first threshold for motion in the region of interest, and/or determining a second threshold for motion in a restricted region outside of the region of interest, wherein the first threshold and the second threshold are independently selected and are independently based on one or more of a clinical application or anatomy sensitivity.

Example 22 may include the method of any one of Examples 19 to 21, further including comparing two consecutive data capture samples to detect motion, and/or comparing a reference data capture sample with a target data capture sample to detect motion.

Example 23 may include the method of any one of Examples 19 to 22, further including determining whether motion by one or more of the object or a component of the medical imaging device is to require a change to one or more of the prescribed scan range or the region of interest, identifying whether motion by one or more of the object or the component of the medical imaging device is to cause a collision event, verifying whether the object is to be in a suitable posture, and/or determining a quiescent period of the object.

Example 24 may include the method of any one of Examples 19 to 23, further including triggering data acquisition based on one or more of an entry to a quiescent period, acceptable motion, compensation for a collision event, or suitable posture, and/or triggering termination of the data acquisition based on one or more of an exit from the quiescent period, unacceptable motion, a failure to compensate for the collision event, or unsuitable posture.

Example 25 may include the method of any one of Examples 19 to 24, further including triggering medication administration based on one or more of an entry to a quiescent period, acceptable motion, compensation for a collision event, or suitable posture.

Example 26 may include the method of any one of Examples 19 to 25, further including compensating for motion of the object to reconstruct the object and generate a final image, defining and/or refining one or more of a motion detection capability, a prediction capability, an acquisition capability, a collision avoidance capability, a posture maintenance capability, a medication administration capability, or an image processing capability, providing supplemental data to a user, and/or providing a message to the user that is to relate to one or more of the motion detection capability, the prediction capability, the acquisition capability, the collision avoidance capability, the posture maintenance capability, the medication administration capability, or the image processing capability.

Example 27 may include the method of any one of Examples 19 to 26, further including utilizing a plurality of detector devices external to the medical imaging device, wherein at least one detector device of the plurality of detector devices generates one or more of a plurality of data capture ranges, a plurality of regions of interest, or a multi-dimensional motion vector field.

Example 28 may include an apparatus to provide motion-gated medical imaging comprising means for performing the method of any one of Examples 19 to 27.

Thus, techniques described herein may provide for an elimination of sedation in subjects (e.g., pediatric patients, etc.). Embodiment may also provide for improved image quality from motion monitoring and/or data acquisition gating. Embodiments may further provide for reduction of multi-slab axial mis-registration artifacts. In addition, embodiments may provide for improved performance of motion compensation processes.

Embodiment may, for example, include an external device for motion vector field generation. Embodiments may also use an external device for consistency between multiple acquisitions in a study. Embodiments may incorporate a scan range into the external device motion monitoring. Embodiment may further reduce "margin" in a scan range due to automatic adjustment of the scan range between scout and CT acquisition.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the computing system within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A; B; C; A and B; A and C; B and C; or A, B and C. In addition, a list of items joined by the term "and so on" or "etc." may mean any combination of the listed terms as well any combination with other terms.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

What is claimed is:

1. An apparatus, comprising:
   a data capture range identifier to identify a data capture range of a sensor device that is to capture motion of an object during a scan process by a medical imaging device,
   a prescribed scan range identifier to identify a prescribed scan range, and
   a detection localizer to focus motion detection to a region of interest in the data capture range based on the prescribed scan range.

2. The apparatus of claim 1, wherein the prescribed scan range identifier is to identify a scan range to be prescribed on one or more of a preliminary image of the object or a scanning table on which the object is located.

3. The apparatus of claim 1, further including a threshold determiner to:
   determine a first threshold for motion in the region of interest, and
   determine a second threshold for motion in a restricted region outside of the region of interest, wherein the first threshold and the second threshold are to be independently selected and are to be independently based on one or more of a clinical application or anatomy sensitivity.

4. The apparatus of claim 1, further including a comparator to:
   compare two consecutive data capture samples to detect motion, and
   compare a reference data capture sample with a target data capture sample to detect motion.

5. The apparatus of claim 1, further comprising:
   an adjuster to determine whether motion by one or more of the object or a component of the medical imaging device is to require a change to one or more of the prescribed scan range or the region of interest;

a collision identifier to identify whether motion by one or more of the object or the component of the medical imaging device is to cause a collision event;

a posture verifier to verify whether the object is to be in a suitable posture; and a quiescent predictor to determine a quiescent period of the object.

6. The apparatus of claim 1, further including a switch to:
trigger data acquisition based on one or more of an entry to a quiescent period, acceptable motion, compensation for a collision event, or suitable posture; and
trigger termination of the data acquisition based on one or more of an exit from the quiescent period, unacceptable motion, a failure to compensate for the collision event, or unsuitable posture.

7. The apparatus of claim 1, wherein the switch is to trigger medication administration based on one or more of an entry to a quiescent period, acceptable motion, compensation for a collision event, or suitable posture.

8. The apparatus of claim 1, further comprising:
a post-processor to compensate for motion of the object to reconstruct the object and generate a final image;
a learner to define and/or refine one or more of a motion detection capability, a prediction capability, an acquisition capability, a collision avoidance capability, a posture maintenance capability, a medication administration capability, or an image processing capability;
a supplemental data provider to provide supplemental data to a user; and
a communicator to provide a message to the user that is to relate to one or more of the motion detection capability, the prediction capability, the acquisition capability, the collision avoidance capability, the posture maintenance capability, the medication administration capability, or the image processing capability.

9. The apparatus of claim 1, further comprising a plurality of detector devices external to the medical imaging device, wherein at least one detector device of the plurality of detector devices is to be used to generate one or more of a plurality of data capture ranges, a plurality of regions of interest, or a multi-dimensional motion vector field.

10. A non-transitory computer readable storage medium comprising a set of instructions, which when executed by a processor, cause the processor to:
identify a data capture range of a sensor device that is to capture motion of an object during a scan process by a medical imaging device;
identify a prescribed scan range; and
focus motion detection to a region of interest in the data capture range based on the prescribed scan range.

11. The non-transitory computer readable storage medium of claim 10, wherein the instructions, when executed, cause the processor to identify a scan range to be prescribed on one or more of a preliminary image of the object or a scanning table on which the object is located.

12. The non-transitory computer readable storage medium of claim 10, wherein the instructions, when executed, cause the processor to:
determine a first threshold for motion in the region of interest; and
determine a second threshold for motion in a restricted region outside of the region of interest, wherein the first threshold and the second threshold are to be independently selected and are to be independently based on one or more of a clinical application or anatomy sensitivity.

13. The non-transitory computer readable storage medium of claim 10, wherein the instructions, when executed, cause the processor to:
compare two consecutive data capture samples to detect motion; and
compare a reference data capture sample with a target data capture sample to detect motion.

14. The non-transitory computer readable storage medium of claim 10, wherein the instructions, when executed, cause the processor to:
determine whether motion by one or more of the object or a component of the medical imaging device is to require a change to one or more of the prescribed scan range or the region of interest;
identify whether motion by one or more of the object or the component of the medical imaging device is to cause a collision event;
verify whether the object is to be in a suitable posture; and
determine a quiescent period of the object.

15. The non-transitory computer readable storage medium of claim 10, wherein the instructions, when executed, cause the processor to:
trigger data acquisition based on one or more of an entry to a quiescent period, acceptable motion, compensation for a collision event, or suitable posture; and
trigger termination of the data acquisition based on one or more of an exit from the quiescent period, unacceptable motion, a failure to compensate for the collision event, or unsuitable posture.

16. The non-transitory computer readable storage medium of claim 10, wherein the instructions, when executed, cause the processor to trigger medication administration based on one or more of an entry to a quiescent period, acceptable motion, compensation for a collision event, or suitable posture.

17. The non-transitory computer readable storage medium of claim 10, wherein the instructions, when executed, cause the processor to:
compensate for motion of the object to reconstruct the object and generate a final image;
define and/or refine one or more of a motion detection capability, a prediction capability an acquisition capability, a collision avoidance capability, a posture maintenance capability, a medication administration capability, or an image processing capability;
provide supplemental data to a user; and
provide a message to the user that is to relate to one or more of the motion detection capability, the prediction capability, the acquisition capability, the collision avoidance capability, the posture maintenance capability, the medication administration capability, or the image processing capability.

18. The non-transitory computer readable storage medium of claim 10, wherein the instructions, when executed, cause the processor to utilize a plurality of detector devices external to the medical imaging device, wherein at least one detector device of the plurality of detector devices is to be used to generate one or more of a plurality of data capture ranges, a plurality of regions of interest, or a multi-dimensional motion vector field.

19. A method comprising:
identifying a data capture range of a sensor device that captures motion of an object during a scan process by a medical imaging device;
identifying a prescribed scan range; and
focusing motion detection to a region of interest in the data capture range based on the prescribed scan range.

20. The method of claim 19, further including identifying a scan range prescribed on one or more of a preliminary image of the object or a scanning table on which the object is located.

* * * * *